(12) United States Patent
Hoogi et al.

(10) Patent No.: US 9,216,008 B2
(45) Date of Patent: Dec. 22, 2015

(54) QUANTITATIVE ASSESSMENT OF NEOVASCULARIZATION

(71) Applicant: TECHNION RESEARCH & DEVELOPMENT FOUNDATION LTD., Haifa (IL)

(72) Inventors: Assaf Hoogi, Maccabim-Reut (IL); Avinoam Bar-Zion, Haifa (IL); Dan Adam, Haifa (IL)

(73) Assignee: Technion Research & Development Foundation Limited, Technion, Haifa (IL)

( * ) Notice: Subject to any disclaimer, the term of this patent is extended or adjusted under 35 U.S.C. 154(b) by 2 days.

(21) Appl. No.: 13/753,747

(22) Filed: Jan. 30, 2013

(65) Prior Publication Data

US 2013/0204127 A1    Aug. 8, 2013

Related U.S. Application Data

(60) Provisional application No. 61/592,068, filed on Jan. 30, 2012.

(51) Int. Cl.
*A61B 8/00*  (2006.01)
*A61B 8/08*  (2006.01)
(Continued)

(52) U.S. Cl.
CPC .............. *A61B 8/0891* (2013.01); *A61B 8/085* (2013.01); *A61B 8/481* (2013.01); *A61B 8/5207* (2013.01); *A61B 8/5276* (2013.01); *G06T 7/0012* (2013.01); *A61B 8/06* (2013.01); *G06T 2207/10132* (2013.01); *G06T 2207/20221* (2013.01); *G06T 2207/30096* (2013.01); *G06T 2207/30101* (2013.01)

(58) Field of Classification Search
USPC .......................... 600/437–469; 382/128–132
See application file for complete search history.

(56) References Cited

U.S. PATENT DOCUMENTS

| 7,657,299 | B2 | 2/2010 | Huizenga et al. |
| 7,729,525 | B2 * | 6/2010 | Camus et al. ................. 382/130 |
| 7,742,629 | B2 * | 6/2010 | Zarkh et al. ................... 382/128 |

(Continued)

OTHER PUBLICATIONS

Behar et al., "The combined effect of nonlinear filtration and window size on the accuracy of tissue displacement estimation using detected echo signals," Ultrasonics (2004), vol. 41, pp. 743-753.

(Continued)

*Primary Examiner* — Sanjay Cattungal
(74) *Attorney, Agent, or Firm* — Daniel J. Swirsky; AlphaPatent Associates Ltd.

(57) ABSTRACT

Systems and methods using contrast enhanced ultrasound imaging for quantitative assessment of neovascularization, such as within a tumor or a plaque. The contrast agent moves in small blotches rather than in continuous flow, but image processing methods enable the detection and quantification of the blood flow, even in the tiny blood vessels of the vasculature tree. The image processing includes compensation for motion of the tissue arising from body movement. The position and extent of the discrete positions of contrast material may be accumulating during a complete heart cycle onto a single 2D image, to enable an indication of a vascular tree based on this local accumulated image. Dynamic processing (DP) of the discrete positions of contrast material enables a complete vascular tree to be obtained. The neovascularization is quantified by the ratio of its total area to that of the plaque in which the neovascularization has grown.

18 Claims, 9 Drawing Sheets

(51) Int. Cl.
*G06T 7/00* (2006.01)
*A61B 8/06* (2006.01)

(56) References Cited

U.S. PATENT DOCUMENTS

| | | | | |
|---|---|---|---|---|
| 8,668,648 | B2* | 3/2014 | Guracar | 600/458 |
| 2003/0032880 | A1 | 2/2003 | Moore | |
| 2007/0058865 | A1* | 3/2007 | Li et al. | 382/173 |
| 2008/0077018 | A1 | 3/2008 | Frijlink et al. | |
| 2008/0200815 | A1 | 8/2008 | Van Der Steen et al. | |
| 2008/0294049 | A1* | 11/2008 | Guracar | 600/458 |
| 2008/0317308 | A1* | 12/2008 | Wu et al. | 382/128 |
| 2009/0187103 | A1* | 7/2009 | Guracar | 600/439 |
| 2010/0081931 | A1* | 4/2010 | Destrempes et al. | 600/437 |
| 2010/0135544 | A1* | 6/2010 | Mattiuzzi et al. | 382/128 |
| 2010/0278405 | A1* | 11/2010 | Kakadiaris et al. | 382/131 |
| 2010/0316277 | A1* | 12/2010 | Fan et al. | 382/131 |

OTHER PUBLICATIONS

Nevo et al, "Automated tracking of the mitral valve annulus motion in apical echocardiographic images using multidimensional dynamic programming," Ultrasound in Medicine and Biology (2007), vol. 33, pp. 1389-1399.

K. Nummiaro, "An adaptive color-based particle filter," Image and Vision Computing (Jan. 2003), vol. 21, issue 1, pp. 99-110.

T.F. Chan and L.A. Vese, "Active contour without edges," by published in IEEE Trans. Image Processing (2001), vol. 10, pp. 266-277.

* cited by examiner

QUANTITATIVE ASSESSMENT OF NEOVASCULARIZATION

CROSS-REFERENCE TO RELATED APPLICATIONS

This application claims the benefit of priority from U.S. Provisional Patent Application No. 61/592,068, filed Jan. 30, 2012, the contents of which is incorporated herein by reference.

FIELD OF THE INVENTION

The present invention relates to the field of the quantification of neovascularization in plaque or in tumors, especially using contrast enhanced ultrasound.

BACKGROUND OF THE INVENTION

Neovascularization is the formation of new blood vessels—generally capillary ingrowth or endothelial proliferation—in unusual sites. The phenomenon is typical of so-called angiogenic diseases, which include angiogenesis in tumor growth. Recently, it has been determined that neovascularization can also occur in arterial plaques. Thus, during atherosclerosis development, reduction of the oxygen supply to the vessel wall may occur, resulting in ischemia, which induces a continual release of growth factors that stimulate the neovascularization processes. These immature neovessels tend to leak and increase the plaque volume, which encourages the ongoing process of neovascularization and the generation of "vulnerable" plaques. Vulnerable plaques, which are also known as "thrombosis-prone plaques," have a high probability of undergoing rupture and causing local thrombosis and embolism, thus leading to stroke. Because of its importance in determining cerebral functionality, the status of the carotid artery is especially important, and carotid atherosclerosis has become recognized as an important factor in the pathogenesis of cerebral events. Some known causes of plaque vulnerability are large lipid core, thin fibrous cap, and calcifications. However, neovascularization and inflammation are generally considered the main causes of atherosclerotic plaque vulnerability and rupture. Inflammatory cells tend to continuously destabilize the plaque by eroding the fibrous cap. This erosion may cause a rupture of the vulnerable plaque, which stimulates platelet aggregation and intravascular thrombosis. A thrombus may detach from the area of the plaque, flow within the internal carotid and block a smaller vessel within the brain Therefore, indication for, for instance, carotid endarterectomy, which is commonly based on the degree of stenosis (>70%), may be insufficient, and risk evaluation based on the plaque composition would be valuable in the treatment decision process. Thus, a noninvasive imaging method to enable the assessment of plaque vulnerability on the basis of plaque vascularization would be highly desirable.

Furthermore, in the treatment of cancerous tumors, many drug therapies operate by attempting to diminish the blood supply to the tumor. Therefore, in common with the above described situation for plaque neovascularization, the quantitative assessment of neovascularization within a tumor is also an important objective which could provide important information for monitoring the treatment of such tumors, and for evaluating potential hazards related to the potential growth of the tumor.

Existing solutions for evaluating the overall size of a tumor or plaque, are generally limited to the determination of some total average of the vasculature dimensions, and are mostly based on ultrasound grey-level imaging using injected contrast agents. However, such a method does not allow any visualization of the vasculature itself. Ultrasound Doppler and Power Doppler technologies do allow imaging of flow, but their spatial resolution is low, since long duration pulses are required. Thus the spatial resolution and the level of information that can be obtained from quantification based on the currently used technologies is limited. Other imaging modalities such as MRI or CT, do not have sufficient resolution to provide specific information about very small blood vessels, besides being less available than ultrasound.

In order to efficiently monitor changes in the vasculature within a tumor or a plaque, it is necessary to identify the vascular tree and to specifically measure its true effective area/volume. The level of quantification currently attained is limited. Neovascularization within plaques has been measured recently, but currently there has been no report of performing this measurement quantitatively. Current methods thus provide only a rough estimate of the amount of contrast agent within a specific area—but such a measure generally lacks the desired accuracy.

In previous studies, visual approaches or gray level averaging within the examined region of interest have been used to semi-quantify intraplaque neovascularization on such contrast-enhanced ultrasound images, usually by using a discrete, limited grading system. Several variations of such visual approach methods have been described in such patent documents as US 2003/0032880 to P. Moore, for Apparatus and Method for Ultrasonically Identifying Vulnerable Plaque, US 2008/0200815 to A. F. W Van Der Steen et al, for Intravascular Ultrasound Techniques, US 2008/007018 to M. E. Frijlink et al., for Pulse Inversion Sequences for Non-linear Imaging, U.S. Pat. No. 7,657,299 to J. L. Huizenga et al., for Automated Methods and Systems for Vascular Plaque Detection and Analysis, and U.S. Pat. No. 7,729,525 to E. Camus et al., for Imaging Evaluation Method for Two-Dimensional Projection Images and Items Corresponding Thereto.

Although such methods and systems provide a general assessment of the neovascularization burden, they lack an objective method for a fully quantitative analysis of neovascularization in atheromatous plaque or in tumorous tissue. There therefore exists a need for providing a method and system able to provide a quantitative measure of neovascularization within a plaque or a tumor, such that enables real time monitoring of the treatment applied to the subject. The carotid artery is a much studied artery and because of its importance, it would be a prime subject for implementing such a method and system. Neovascularization in plaques therein will therefore be generally used in this disclosure to illustrate exemplary implementations of the various aspects of the methods and systems described herewithin. It is to be understood, however, that it is not intended that the methods and systems described and claimed be limited to this specific example.

The disclosures of each of the publications mentioned in this section and in other sections of the specification, are hereby incorporated by reference, each in its entirety.

SUMMARY OF THE INVENTION

The present disclosure describes new exemplary systems and methods for quantitative assessment of neovascularization, such as within a tumor or a plaque. The systems and methods use contrast enhanced ultrasound imaging, but incorporate image processing methods to enable the detection and quantification of the blood flow, even in small blood vessels of the vasculature tree. The method is fraught with a number of major problems, which are solved by the methods and systems of the present disclosure. In the first place, a problem of spatial resolution exists. The size of the neovessels can be very small—of the order of 10 to 50 microns. The common imaging tools used, such as CT, MRI and Pet-Spect, can not reasonably resolve such small diameters. However, using Contrast Enhanced Ultrasound (CEUS) with contrast agents, much better spatial resolution can be obtained, which enables the imaging of those vessels. Furthermore, the motion of the lumen itself with time may be many times larger than the tiny flow movements sought in the small vessels of the tumor or plaque. Such movement may include involuntary movement of the patient, such as swallowing or coughing. Even more importantly, the heart's pulse itself causes large discrete pulses of blood to flow through the arteries, whose pressure can compress or move a plaque periodically during every pulse.

The contrast enhanced ultrasound technique involves the injection of a contrast enhancing medium into the patient's blood stream. The effect of the impinging ultrasound on such a contrast medium is to activate the small gas bubbles, typically of a 1-3 μm in diameter, and these reflect the ultrasound waves efficiently, whereas the blood itself does not. However, the contrast enhancing agent is spread out into discrete and isolated locations in the blood stream, such that the blood vessel in which it is imaged appears like an intermittently dashed line. The main reason for the discrete blobs may be the very high resistance of the tiny intra-plaque neovessels. The system and methods described in this disclosure are capable of distinguishing between the ultrasound reflections from the contrast material flowing in these small blood vessels, and the ultrasound reflections from the surrounding tissue due to harmonic imaging. The body tissues generate echoes at mostly the fundamental frequency of the transmitted ultrasound frequency (in harmony with the original transmitted frequency). On the other hand, the contrast agents, due to their nonlinear behavior, can also produce sub-harmonic and second-harmonic frequencies, thus enabling imaging of the contrast enhancing medium and reconstruction of its flow path.

A number of methods are described to enable the generation of more continuous images of the vasculature from the echoes generated from discrete points along the paths of the vessels of the vasculature tree. These methods result in a picture of the vasculature tree in significant detail in two dimensions, with indications also of the three dimensional structure.

The system and methods used involve at least three important processing elements:
(i) compensation for motion of the region of interest (ROI), where the term motion is defined as comprising any of, or a combination of translation, rotation and scaling.
(ii) segmentation, meaning the outlining of the position and extent, of discrete contrast spots appearing during a heart cycle, accumulating and projecting them on a single 2D "accumulation" image, to obtain an indication of a vascular tree based on this local accumulated image, and determination in this accumulated image of the total intra-plaque area of the neovascularization and its load on the plaque.
(iii) determination of a complete vasculature tree by the use of dynamic processing (DP) of the discrete positions of contrast material, and determination of the total intra-plaque area of the neovascularization and its load on the plaque.
The quantification of the neovascularization extent can be performed from the vascular tree of the type determined either in step (ii), or in step (iii), or in a combination thereof, namely performing DP on the data obtained from the accumulated image.

Use is made of input data from the ultrasound imaging system, as acquired by the ultrasound probe in the form an image or image sequences, using time sequences of the ultrasound data of acquired 3D volumes. It is to be understood that the term image in the present disclosure is intended to include either the data making up an image in the system memory, or a physical image itself as projected onto a monitor for review by attending medical personnel. The data is processed either fully automatically or with human operator assistance to increase accuracy. Initially, it is necessary to define the region of interest (ROI) of the tumor or plaque. The movements of the ROI are then followed during a predetermined period of time, and compensation is applied for translational, rotational and change of scale movement of the ROI. Such movement could be generated by movement of the ROI relative to the position of the US transducer, such as, in the exemplary case of the carotid artery, as a result of the patient swallowing, or from the natural pulsation of the region due to the pulse in the main artery.

Within the ROI itself, the echoes arising from the contrast agent within the blood vessels may then be separated from those of the surrounding tissue. The different pixels or voxels or segments representing echoes defined as coming from the contrast agent, are separated from background signals over time or space/volume, to form the basis for calculating any continuous paths between the discrete segments of the imaged contrast material. A construction of all of these paths is a complete tree of arterioles. Of course, the pixels which may be determined as coming from the contrast agent may be so few and scattered, that there may be no possibility of constructing any continuous path, indicating a clinically insignificant level of neovascularization, or there may be essentially none detected, such that an essentially zero level of neovascularization is indicated.

Several logical decision procedures may be used to enhance the probability that several segments or pixels/volumes are positively included within a branch of the arteriole tree. The area and/or volume of blood/contrast agent contained within the lumen of the arterioles that form the arteriole tree is then estimated. In addition, the orientation of the flow over time is calculated, as part of the delineation process of the shape of the arteriole tree. As a result of executing the above described steps, a description may be obtained, in 2D or 3D, of the arteriole tree within the ROI of the tumor or plaque, together with the calculated volume of that tree. The reconstruction of a 3D arterial tree may be more accurate than the 2D analysis because it is less dependent in the imaged cross-section and in the location of the ultrasound probe, thus supplying more reproducible results. The process includes monitoring of different 2D cross-sections of the plaque or tumor, and reconstructing those sections over a whole area. Additionally, it is possible to obtain shape parameters such as the length of the branches and the branching morphology of the vessels within the tumor or a plaque.

The above described method, in all of its implementations, can be utilized as part of the image processing routines of the ultrasound imaging system, or as a stand-alone post-processing package, and provides clinicians with novel screening and monitoring capabilities in the diagnosis and treatment of disease. It allows clinicians who diagnose or treat patients with cancerous tumors to assess the potential rate of growth of the tumor, and its response to anti-angionetic therapy; it allows clinicians who assess the vulnerability of plaques to do so in a quantitative manner; and it allows for the screening of patients who may be susceptible to stroke or acute myocardial infarction.

There is thus provided, in accordance with an exemplary implementation of the methods described in this disclosure, a method of analyzing ultrasound images to provide information regarding neovascularization in a tissue of a subject, the method comprising:
(i) obtaining a series of contrast enhanced ultrasound images of the tissue,
(ii) compensating for motion of tissue features between different ones of the contrast enhanced ultrasound images, to generate a series of compensated images,
(iii) detecting in at least one of the compensated images discrete segments of imaged contrast material,
(iv) constructing a representation of an arterial tree from the detected segments,
(v) quantifying the level of the neovascularization from the extent of the detected segments in the representation of the arterial tree.

In this method, the representation of the arterial tree may be constructed by superimposing the positions of the discrete segments of the imaged contrast material from at least two sequential ones of the compensated images, to generate an accumulated image, and detecting segments on the accumulated image. The representation of the arterial tree may be constructed by performing dynamic programming either on at least one of the series of compensated images, or on the accumulated image. The resulting the arterial tree should comprise at least one continuous path between the discrete segments.

In other implementations of this method, the quantifying may be performed by determining the ratio of the extent of the detected segments in the arterial tree to the imaged area of the tissue in which the neovascularization is to be determined.

Additionally, the step in these methods of compensating for motion of features between different ones of the images may performed either by forward tracking or by particle filtering methods. In the former case, the method may utilize template matching with a normalized cross correlation criterion. In the latter case, the method may utilize a Sum of Absolute Differences (SAD) criterion for each particle.

In any of the above described methods, the motion of tissue features may comprise at least one of translation, rotation and change of scale of the features. Additionally, in any of these methods, the tissue may be either a plaque or a tumor.

Still other exemplary implementations involve a system for providing information regarding neovascularization in a tissue of a subject, the system comprising:
(i) an ultrasound system for generating a series of contrast enhanced ultrasound images of the tissue,
(ii) a frame analysis unit receiving the images and adapted to designate locations within the images showing the presence of contrast material,
(iii) a motion compensating unit, configured to output a series of compensated images in which the effects of motion of imaged features of the tissue between different ones of the images is cancelled, and
(iv) an image processing system comprising:
  (a) a segment detector unit, adapted to detect in at least one of the compensated images discrete segments of imaged contrast material, and
  (b) an arterial tree constructor for outputting a representation of an arterial tree from the detected segments, and
(v) an output unit using the extent of the detected segments in the representation of the arterial tree to quantify the level of neovascularization in the tissue.

In such a system, the arterial tree constructor may be configured to superimpose the positions of discrete segments of the imaged contrast material from at least two sequential ones of the compensated images, to generate an accumulated image, and to detect segments on the accumulated image. Additionally, the arterial tree constructor may be configured to perform dynamic programming either on at least one of the series of compensated images, or on the accumulated image. The resulting the arterial tree should comprise at least one continuous path between the discrete segments.

In other exemplary implementations of such systems, the output unit may be adapted to quantify the level of neovascularization in the tissue by determining the ratio of the extent of the detected segments in the arterial tree to the imaged area of the tissue in which the neovascularization is to be quantified.

Additionally, the motion compensating unit may be adapted to cancel the effects of motion of imaged features of the tissue between different ones of the images by performing either one of forward tracking or particle filtering methods. In the former case, the method may utilize template matching with a normalized cross correlation criterion. In the latter case, the method may utilize a Sum of Absolute Differences (SAD) criterion for each particle.

In any of the above described systems, the motion of tissue features may comprise at least one of translation, rotation and change of scale of the features. Additionally, any of these systems may be adapted to provide information regarding neovascularization in either a plaque or a tumor.

BRIEF DESCRIPTION OF THE DRAWINGS

The present invention will be understood and appreciated more fully from the following detailed description, taken in conjunction with the drawings in which.

DETAILED DESCRIPTION OF THE INVENTION

Figure 1:
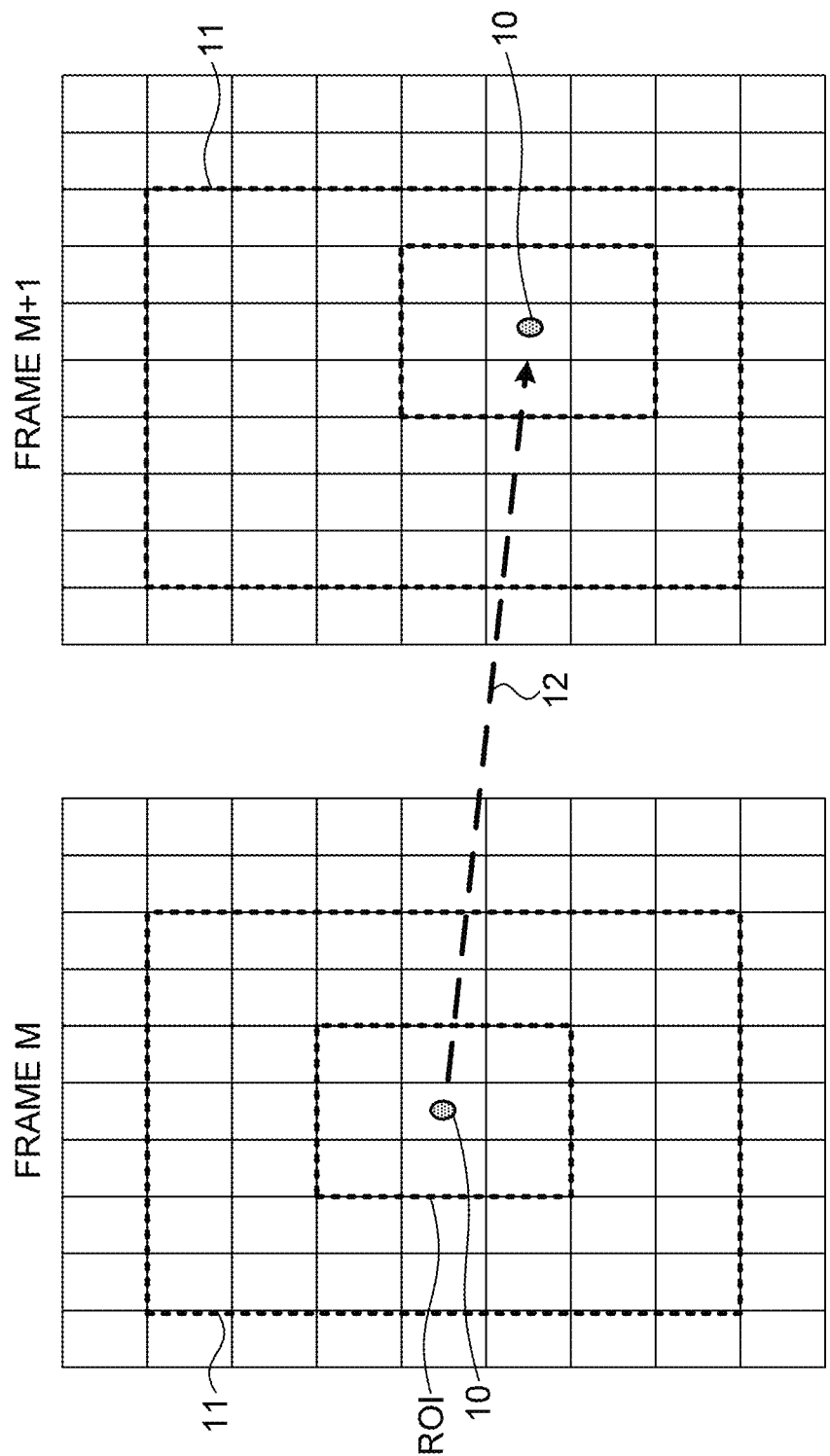
FIG. 1 shows one method of applying motion compensation to successive frames of ultrasound images of a region under examination.

Exemplary systems and methods for quantification of neovascularization, as described in the present disclosure, involve the acquisition of contrast enhanced ultrasound (CEUS) images in the region where the neovascularization is to be calculated. Ultrasound examination of the carotid bifurcation and internal carotid artery is used as an exemplary application of the methods of this disclosure. Typically, a routine ultrasound grayscale image procedure is performed to assess the position, size and shape of the plaque (if neovascularization in a plaque is being measured), followed by color and spectral Doppler imaging to confirm the degree of stenosis. This can be performed, for instance, on an iU22 ultrasound system, available from Philips Healthcare of Bothwell, Wash., with a 4-8 MHz broad band linear array transducer. Thereafter the activated contrast agent, such as Definity™ as supplied by Bristol-Myers Squibb Medical Imaging Corp., of North Billerica, Mass., diluted in saline, is injected, preferably by bolus injection, and the CEUS imaging is performed. The bolus injection may be advantageously performed in two identical sequences, each one delivering half of the solution. Injection may be slowly performed, followed by injection of 5 ml of normal saline to flush the vein. The time delay between the sequential injections may be about 3 minutes, allowing the first solution to be flushed before performing the second injection, thus preventing the first injection from affecting the results of the second bolus. Contrast ultrasound power is then applied, with enforced relatively low Pulse Repetition Rate (12 Hz) and low mechanical index (0.07) to avoid early bubbles destruction. Pulse inversion is also used to optimize depiction of intravenous contrast and minimize echoes from the surrounding tissues. Cine loops are recorded of the region of interest, which, as stated above, uses the carotid artery as an example to illustrate the method, though it is to be understood that the method is not intended to be limited thereto. The cine loops are recorded starting from the time the contrast agent is seen in the carotid lumen and extending for a number of heart cycles, typically approximately five. The loops should be acquired while holding the transducer over the plaque to be quantified. The longitudinal cross-section is chosen according to the best obtained images of the plaque.

The cine loops acquired during each clinical examination may be transferred, typically as DICOM files, to a computer workstation for off-line post-processing, or may be analyzed in the Ultrasound System's own computing system. The images may be analyzed according to the methods described in this disclosure, using a suitable software suite, such as Matlab, available from The Mathworks Inc. of Natick, Mass. Cines which include images with heavy calcified plaques, which cause acoustic shadowing during the CEUS imaging, are excluded from the analysis. Cines with significant movement, such as is caused by the patient swallowing, should also be ignored. On the other hand, frames in which the plaque and its neovascularization are clearly visualized, may be readily measured.

Motion compensation is first applied in order to separate contrast agent flow from the movement of the surrounding tissues. Two exemplary methods can be used for this purpose. A first method uses forward tracking, using block matching with a normalized cross correlation (NCC) criterion, as described in the article entitled "The combined effect of non-linear filtration and window size on the accuracy of tissue displacement estimation using detected echo signals" by Behar et al., published in Ultrasonics (2004) vol. 41 pp. 743-753, and in the article entitled "Automated tracking of the mitral valve annulus motion in apical echocardiographic images using multidimensional dynamic programming" by Nevo et al, published in Ultrasound in Medicine and Biology (2007) vol. 33, pp. 1389-1399, both herewith incorporated by reference in their entirety. A second possible method uses a particle filter method, as will be further explained below. Before applying either method, a region of interest (ROI) included the plaque is defined. Each method has advantages and disadvantages in its ability to track the displacement of this ROI between sequential frames.

The first method is now described with reference to FIG. 1, showing two successive frames marked Frame M and Frame M+1. Given a sequence of 2D images, the point 10 to be tracked in the reference image, Frame M, is selected, and a region-of-interest, ROI, is defined around it. The ROI is defined by the 3×3 pixel square shown outlined by the small dots in the frames of FIG. 1. The displacement of the selected point 10 is estimated by comparing the selected ROI to all possible same-sized ROIs in a predefined search area 11, shown by the large square-dashed outline in FIG. 1, in later frames such as Frame M+1, allowing a predetermined displacement for each direction between sequential frames. As is observed, in Frame M+1, an identically sized ROI has been found with the tracked point 10 in the same position (the center) relative to the ROI as in Frame M. The position of the point tracked 10 has thus been defined in Frame M+1 displaced 1 pixel to the right and 1 pixel downwards (in the sense of the drawings of FIG. 1) relative to its previously found position in Frame M, the displacement being designated by the arrow 12. The predetermined displacement between sequential frames is limited to a step size sufficiently small to prevent large undesired and non-physiological movements, such as swallowing, from interfering with the procedure. For each examined shift, the similarity of the patterns between the ROIs (Frame M and Frame M+1) is estimated by normalized cross correlation (NCC). The NCC is chosen due to its insensitivity to variations in the image gray levels. The shifts which provide the highest value of the NCC function are considered as the most likely displacement of the chosen ROI between those frames.

The second method, a particle filter method, may lead to an optimal solution when dealing with non-linear and non-Gaussian models for tracking of non-rigid objects, as is known in the art, such as in the article by K. Nummiaro, et al., entitled "An Adaptive Color-Based Particle Filter", published in Image and Vision Computing, Vol. 21, Issue 1, pp. 99-110, January 2003. The particle filter method assumes that the rotation-translation-scaling transformation parameters are not equally distributed, nor are they predefined. For every frame k, a large set of random vectors are drawn according to these probability functions. For each vector or particle $$(\alpha, \beta_x, \beta_y, \Delta x, \Delta y)_l \; l \in 1, 2, \ldots L,$$

where L is a determined number of drawn vectors, the parameters $\alpha, \beta_x, \beta_y$ are used for a rotation-scaling-transformation of $ROI^{k-1}$. $ROI^k$ is defined by the center of $ROI^{k-1}$ plus drawn $\Delta x, \Delta y$. The matching quality is calculated according to the Sum of Absolute Differences (SAD) criteria:

$$SAD_l(\alpha, \beta_x, \beta_y, \Delta x, \Delta y) = \minarg \sum_{x,y \in D} (ROI_{\alpha, \beta x, \beta y} - ROI^k)$$

Using the SAD of each particle, a weight for each particle can be calculated:

$$w_l = e^{-SAD_l/mean(SAD)}$$

Thus, a set of parameters that express the movement of the plaque between sequential frames can be estimated as the weighted sum of the vectors:

$$(\alpha, \beta_x, \beta_y, \Delta x, \Delta y) = \frac{1}{L} \sum_l (\alpha, \beta x, \beta y, \Delta x, \Delta x)_l \cdot w_l$$

Either of these two exemplary methods, or any other suitable method, may be used to compensate for motion of the ROI between frames. Both of the above described methods generally produce similar results, but the computation time using the particle filter method is expected to be higher.

Figure 1A:
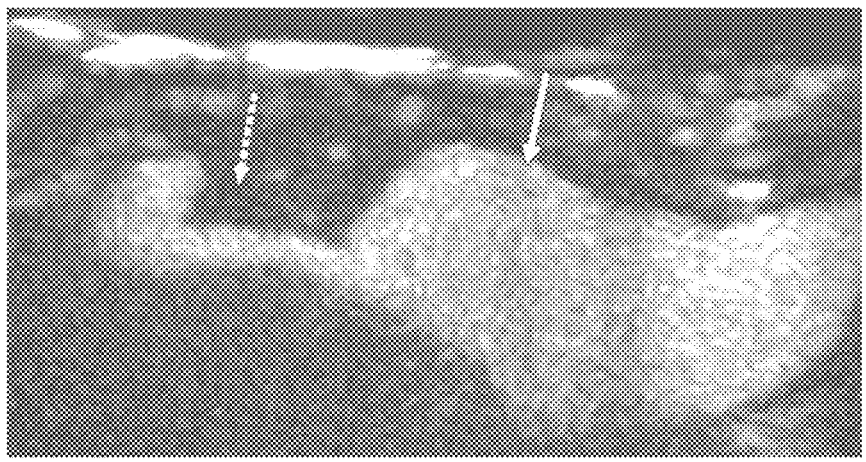
FIGS. 1A to 1C are ultrasound images taken of a plagued region of a carotid artery, to illustrate how the image processing methods of the present application may be performed.
Figure 1B:
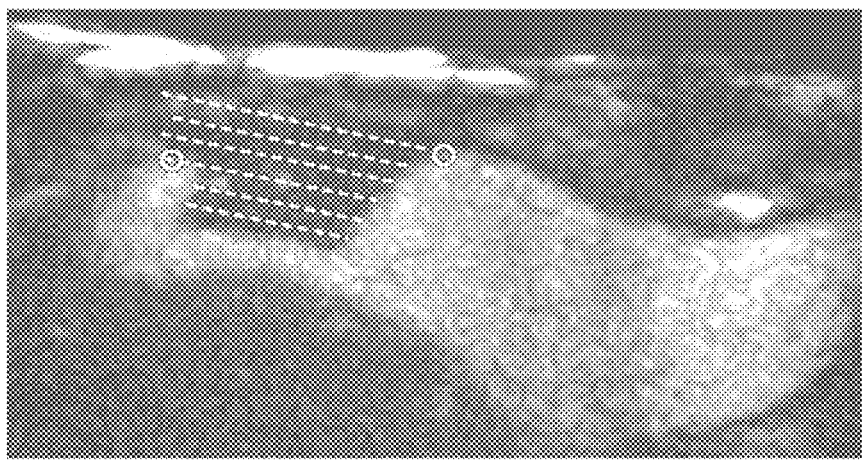
Figure 1C:
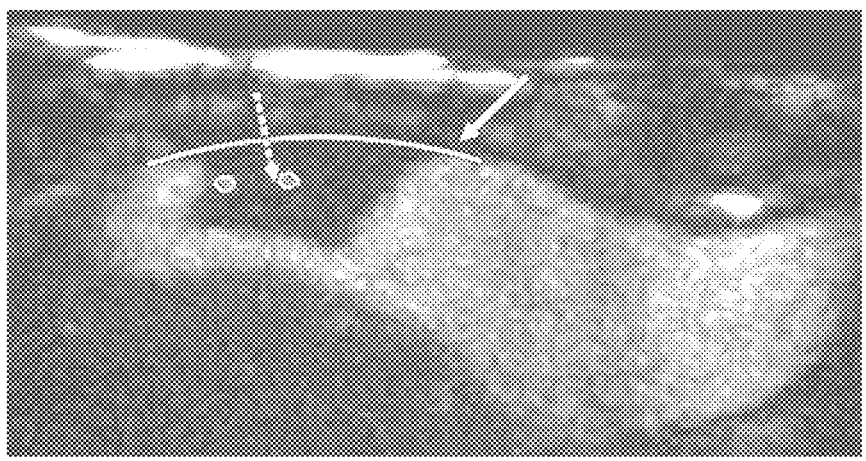

Detection of the intra-plaque neovascularization now begins by defining the region of the entire plaque by image analysis of the image frames, and determining the plaque area. In general, after sufficient time has elapsed for the contrast agent to reach the region to be examined, the plaque is identified by a region having little or no contrast. The borders of the plaque have to be detected, including its base. One advantageous method of delineating the borders of the plaque is by fitting a parabola through the edge points, taking into account the orientation of the arterial wall. Reference is now made to FIGS. 1A to 1C, which are ultrasound images taken of a plaque region of a carotid artery, to illustrate how this image processing procedure may be performed.

In FIG. 1A, there is shown the carotid artery, labeled with the solid white arrow, which provides a good echo signal from the contrast enhancing material flowing therein, as shown by the light colored region. Because of the almost complete absence of blood flow within it, the plaque is seen as a dark region, indicated by the dashed arrow. As is observed, some small regions of contrast material are seen within the plaque as small light colored blotches, these arising from discrete regions of contrast material travelling down the small neovascularization vessels within the plaque, which it is the object of the systems and methods of this disclosure to plot and quantify. A segmentation process, such as that based on an active contour model, as described in the article by T. F. Chan T F and L. A. Vese entitled "Active contour without edges" published in IEEE Trans. Image Processing, V.10, pp. 266-277, (2001) may be used to delineate the contrast enhanced carotid artery.

Reference is now made to FIG. 1B, which illustrates how the area of the plaque may be calculated from this image, according to one exemplary method, by drawing lines parallel to the long axis of the lumen through the longitudinal extent of the plaque, as shown by the dashed lines. The intersections of these lines with the contrast enhanced lumen artery are measured. For each end of the plaque, the last line that still crossed the contrast enhanced lumen of the artery provides the edge points of the plaque, indicating its longitudinal extent, as shown by the two exemplary circles in the image.

Reference is now made to FIG. 1C, which illustrates how the base of the plaque may be delineated by fitting a parabola through the edge points found in FIG. 1B, taking into account the orientation of the arterial wall, as shown by the solid white arrow in the image of FIG. 1C.

The neovascularization within the defined plaque region is now detected by observing the presence of the contrast agent flowing through the neovascularization vessels. These regions are shown in FIG. 1C by the white circled regions as indicated by the dashed arrow. An automatic segmentation routine may be applied to these contrast-enhanced regions within the plaque in each frame, such as by the above referenced Chan and Vese method. Contrast-enhanced areas detected outside the defined plaque region should be deleted to avoid erroneous processing of the frame. A label is assigned to every pixel in each image, such that pixels depicting part of the enhanced flow regions are distinguished from the background plaque regions. The ultrasound technician can optionally examine and manually correct the results of the automatic segmentation process, if it is seen that obvious misinterpretations have arisen. In each frame of the sequence, the contrast agent appears in the images as a series of accumulated clusters at different locations along the detected blood vessel, instead of the expected continuous flow line along the blood vessel. A possible reason for this, as proposed in the prior art, is that the clustering may arise because of the high resistance of the narrow vessels. Alternative suggested reasons are because of low forced PRF of the ultrasound imaging beam or out-of-plane flow inside the vessels, or because the contrast agent concentration is relatively low and the agents aggregate. However, it is to be understood that the methods of the present disclosure are applicable regardless of the reason for the clustering. An "accumulation" process is then performed by integrating the final neovascularization segments in each frame region over all the chosen frames acquired during the cardiac cycle. A mean between the results in sequential cycles may then be calculated. Once the mean of the accumulated areas of neovascularization segments has been determined, the resulting path of the revealed vessel or vessels shows the neovascularization tree, based on analysis of the actual accumulated image. Using this image, it is possible to calculate the ratio of the neovascularization area to the total plaque area, which, for instance, provides the physician with the sought-after information regarding the extent of neovascularization.

In order to automatically reconstruct the full neovascularization route, and to isolate different intra-plaque neovascularization routes when more than one is detected, as is the usual situation, a dynamic programming (DP) method may be implemented. This procedure is able to construct a computed neovascularization tree based on the computer synthesis of the path of the vessels using DP. In general, dynamic programming provides an efficient way of finding an optimal connective path, using minimization of a cost function, as is known in the art. For this application, the cost function depends on predefined parameters such as the step size allowed along the axes, the continuity and the smoothness of the curve, and the preference as towards which type of neighboring pixel the curve should proceed. The smoothness of the curve is ensured by calculating the spatial derivative along the route. The spatial derivative can be either the first derivative or the second, depending on the function. In order to find an initial branching point along the vessel path, a first derivative is preferred. In order to discriminate against centroids not related to the path being currently plotted, a second derivative may be used. In addition, light colored pixels are preferred over dark colored ones, so that the path construction preferentially proceeds, all other factors being equal, towards a neighboring light colored pixel rather than a dark colored pixel, to include as many light colored pixels (representing the contrast medium) as possible in the path.

Reference is now made to FIGS. 2A to 2D, which are frames taken from the sequence shown in FIGS. 1A to 1C above, to first illustrate graphically how the overall procedure is performed. A more detailed explanation is given hereinbelow, in reference to FIGS. 5A-B and 6A-B.

Figure 2A:
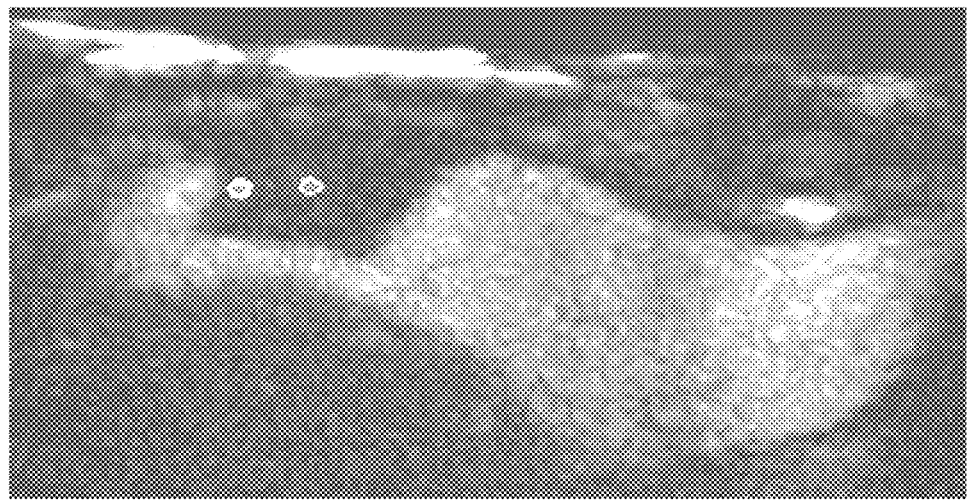
FIGS. 2A to 2D are frames taken from the sequence shown in FIGS. 1A to 1C, to illustrate graphically how the overall procedure is performed.
Figure 2B:
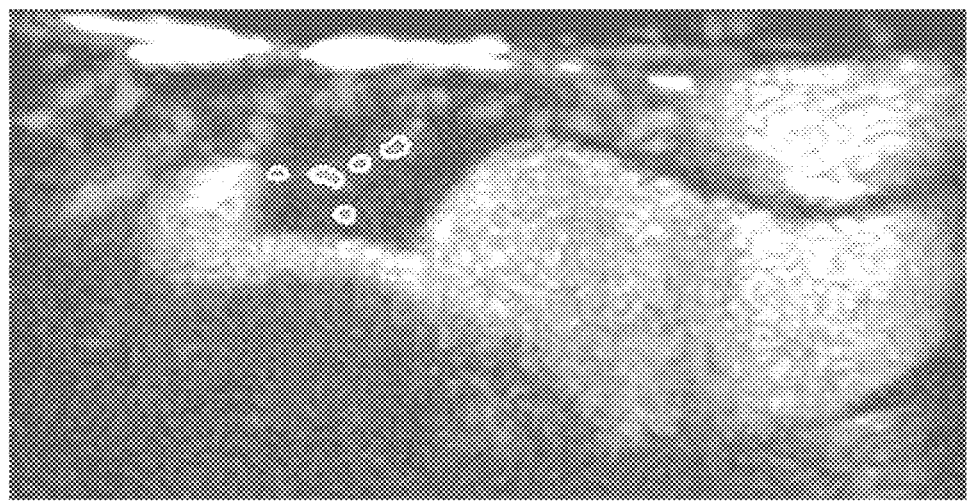

FIGS. 2A and 2B show the intraplaque neovessels during different phases of the heart cycle, showing qualitatively how different segments of the vessel paths can be imaged as the discrete contrast enhanced regions flow through the vessels. FIG. 2A shows a single vessel denoted by the two blotches of contrast material, emphasized by the white boundaries added to them in the image, while in FIG. 2B, taken at a later point in the heart cycle, the vessel is seen probably to have branched into two sub-vessels.

Figure 2C:
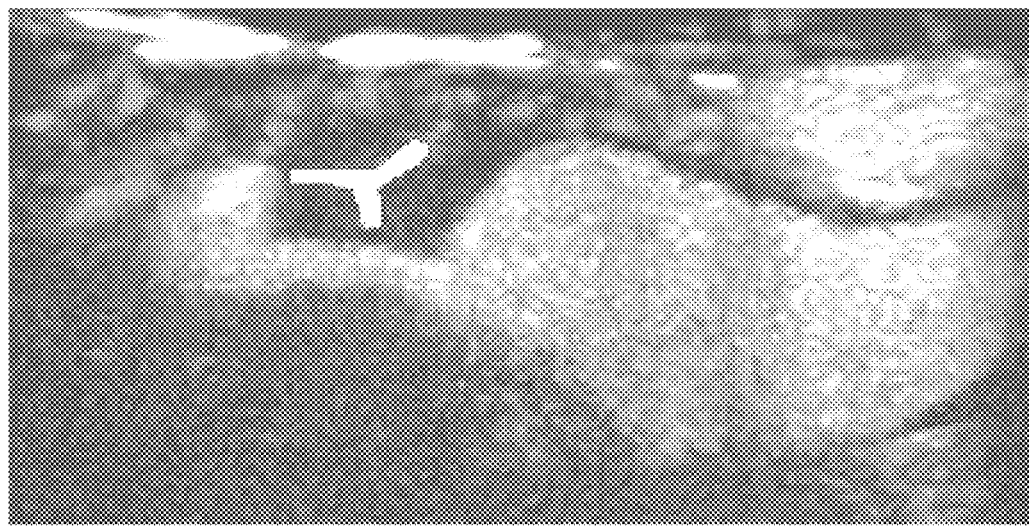
Figure 2D:
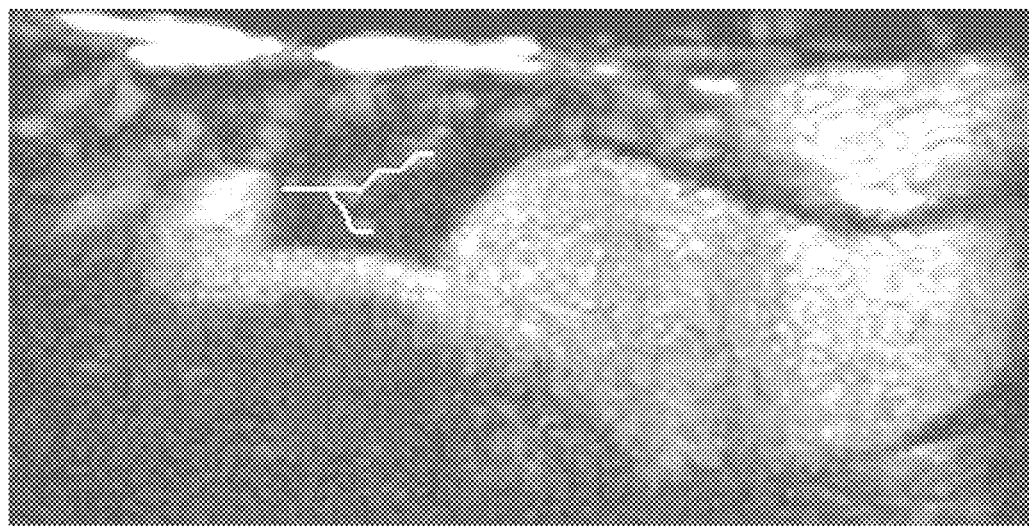

FIG. 2C shows an example of a continuous intraplaque neovascularization revealed after the accumulation procedure has been performed for sequential frames during the entire heart cycle. In the event that the accumulation process does not result in such a display of entire arms of the neovascularization tree, but that only discrete isolated regions of contrast material are imaged, then a 2-dimensional reconstruction of neovascularization routes has to be performed, advantageously using the dynamic programming (DP) methods described hereinbelow, resulting in an output of a representation of parts of the vascular tree, as shown in FIG. 2D.

Figure 3:
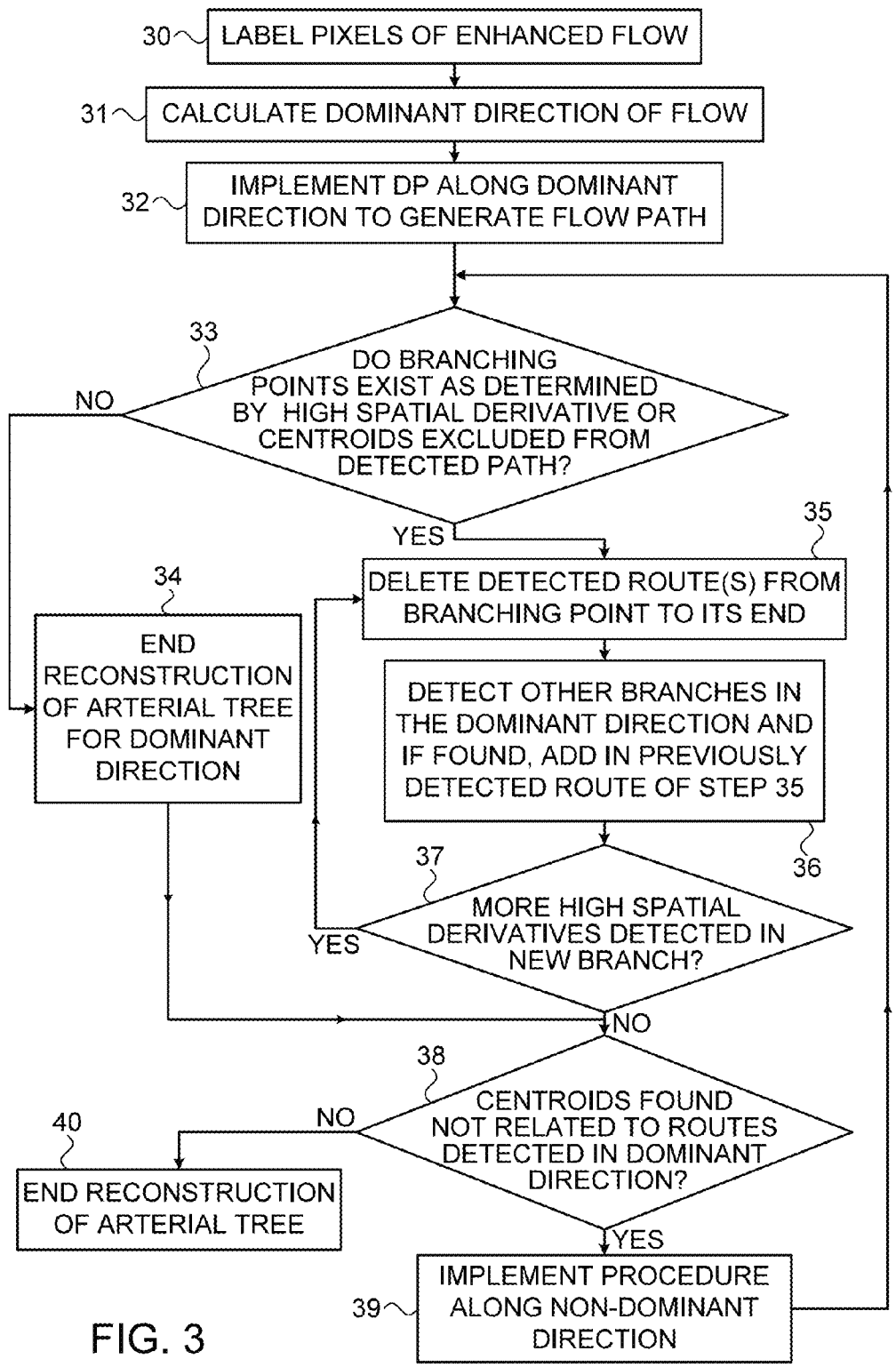
FIG. 3 illustrates schematically one possible method by which the reconstruction of a complete arterial tree can be made from the frames showing disconnected segments of CEUS flow.

Returning now to the detailed procedure of a dynamic programming routine, as stated above, after detecting the intra-plaque neovascularization regions and performing the "accumulation" process over a sequence of images, the resultant image may still include disconnected segments of CEUS flow. Reference is now made to FIG. 3, which illustrates schematically one possible method by which the reconstruction of the complete arterial tree can be made from the frames showing such disconnected segments of CEUS flow. The implementation of the flow chart of FIG. 3 is illustrated in actual examples of flow reconstruction shown in FIGS. 4A to 4D.

The first step 30 of the method of FIG. 3 involves the labeling of the pixels constituting the regions of enhanced flow in each frame.

In step 31, the dominant direction of the flow associated with these pixel labels is calculated. Dynamic Programming is then implemented in step 32 along this dominant direction to attempt to correlate the sequences of the various pixel labels in successive images to generate a complete path from these labels.

In step 33, branching points of the vasculature are located, as characterized by either or both of (i) high values of the slope of the curve of the flow path, and (ii) the existence of further labels which have not been included along the detected route. The level at which the first derivative of the curve is considered to represent a potential branching point is set at a predetermined level for each case.

If neither such high first derivative, nor any excluded labels are detected, the reconstruction of the intra-plaque arterial tree is presumed to be completed in that single direction, as shown in step 34. However, in case there are other centroids in the image unconnected to this first determined path in the dominant direction, a search should be made for such centroids in the non dominant direction, and the process is continued in step 38. The resulting image can be output to the technician for review before calculation of the neovascular volume is performed, if required.

On the other hand, if either or both of the effects shown in step 33 are detected, it is then necessary to determine the path of the branch artery, if indeed present. This may be performed by first deleting the so-far detected route in the dominant direction, from the branching point to the furthest label detected, as indicated in step 35.

Then, in step 36, the process begins of detecting the branch artery path from the point in the path showing the high spatial derivative, by searching for labels other than those related to the so-far detected (and now deleted) route, according to the procedure described in step 32. If none are found, it is concluded that there are no further branches from that point of high spatial derivative detected in step 33, and that the high spatial derivative was an anomaly. If a further branch was detected, then at the conclusion of step 36, the originally detected flow path is restored, in addition to its newly determined branch. In step 37, as search is made for high spatial derivatives in the newly determined branch, and if found, the procedure for detecting further branches is reinstituted as per step 35.

If no further high spatial derivative points are found, then in step 38, a search is performed for additional centroids not included in the so-far detected paths and their branches along the dominant direction.

If other labels are detected, it is assumed that these must arise from another branch or branches, and the DP is implemented along the non-dominant direction in order to track the path of that branch, as shown in step 39. The tracks derived in both these scanning traverses can then be combined to derive a more complete vascular tree.

If on the other hand, no further centroids are detected in step 38, then it is deduced that the construction of the intra-plaque vascular tree is complete, as shown in step 40, and the results can be outputted from the system.

Figure 4A:
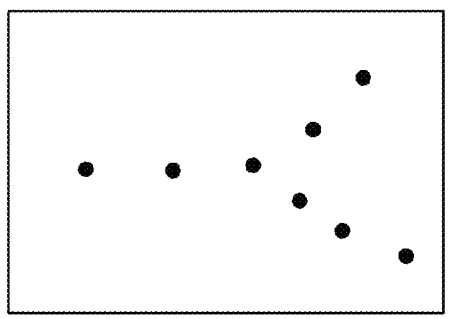
FIGS. 4A to 4D illustrate pictorially the main steps of the implementation of the method shown in the flowchart of FIG. 3.
Figure 4B:
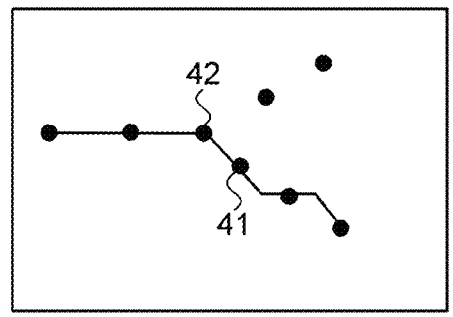

Reference is now made to FIGS. 4A to 4D, which together illustrate pictorially the main steps of the implementation of the arterial tree reconstruction method shown in the flowchart of FIG. 3. In FIG. 4A, the centroids of all the detected segments are shown, and in order to determine the dominant direction, the difference between the first (left) centroid and the last (right) one is measured along each axis, x and y. In the example image shown in FIG. 4A, the x-direction (horizontal in the drawings) is seen to be the dominant direction since it has the larger difference. DP is then implemented along the x-direction, this being assumed to be the dominant orientation of the vasculature. The DP proceeds, scanning the image step by step, and connecting each centroid to the closest one in the dominant direction. The result of the DP for this example is shown in FIG. 4B, from which it is observed that at the point 42, where there were two centroids to chose from as the next point in the path, the closer one—the lower one 51 in FIG. 4B—was chosen. The method continues plotting the path along the lower set of centroids.

Figure 4C:
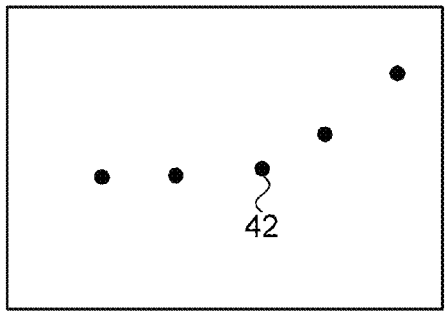
Figure 4D:
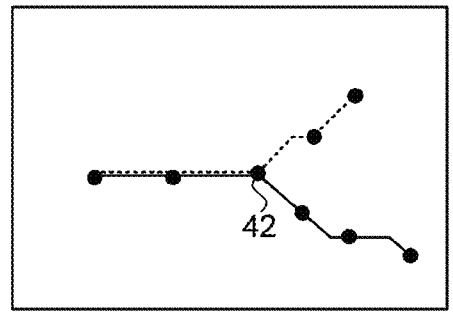

Since the detected path did not pass through all the labels in the image, a search is then commenced for a location along the path plotted so far, characterized by a high first spatial derivative, where the criterion as to what is considered a "high" first spatial derivative should be predetermined according to the characteristics of the case being analyzed. Such a location may potentially be a branching point of two or more vessels. In FIG. 4B, a high first spatial derivative is detected at point 42 and it is assumed that there is a branch initiated at that point, and that any excluded labels should be located in the vicinity of that point. In order to include them, the previous path is deleted from the image, from the assumed branching point 42 to the end of the initially found path, the remaining labels then probably indicating a path leading to at least another branch of the tree. This is illustrated in FIG. 4C. A new DP cycle is implemented to detect, with high likelihood, the route of this new neovascularization path, representing the flow to the branch vessel. The result of this new DP cycle is the plotting of the upper branch from the branching point 42, shown in FIG. 4D as a dashed line. Additional branching points may also be found. Combination of all of the paths detected, as shown in FIG. 4D for the two previously plotted paths, results in the plotting of the entire neovascularization tree.

According to an alternative method of performing the DP path determination, it is possible to perform a second plot in the less dominant direction if it is observed that any labels have been omitted in the dominant direction plot, and then to combine the tracks derived in these two scanning traverses.

In order to validate the performance of the described method and the system for implementing it, studies were conducted to compare the results obtained by application to a specific case of a carotid arterial plaque, with the results obtained on the same plaque using manual marking as performed by two unbiased observers. The validation was performed to assess the accuracy of the two main steps of the method, namely (i) motion compensation and (ii) reconstruction of the arterial tree. The validation procedure was performed on a number of plaques in different patients.

The validation of the motion compensation step was performed by marking manually two points that defined the plaque base. Global plaque movement between sequential frames was determined by averaging the displacements of these base points. The results of the two semiautomatic methods were compared to the results of each observer. This process was implemented for all patients. The average and the Standard Deviation values were calculated. The results showed that the method was sufficiently acceptable as a quantifier of the motion compensation arising from the heartbeat. In order to determine the efficiency of the semi-automatic methods, the computation time was also calculated.

The spatial accuracy of the reconstructed arterial trees was evaluated by comparing the results obtained using the methods described hereinabove, to those produced by observers who marked the locations of the intra-plaque enhanced regions, and connected them visually as continuous routes. Several error parameters were calculated:
a) the mean distance between any route branch detected manually and the same one detected automatically,
b) the maximal distance between them,
c) the length of each route, and
d) the slope of each route.

For each parameter, the mean, the standard deviation values and the range of the results were calculated for the whole patient population studied.

Figure 5A:
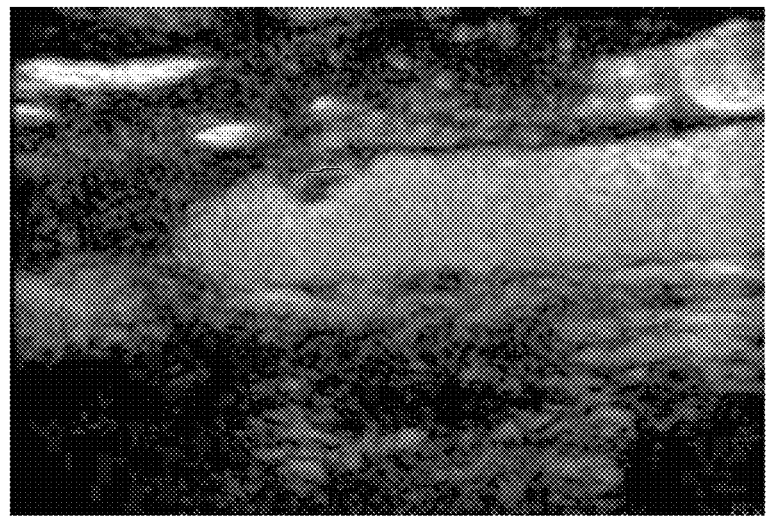
FIGS. 5A and 5B present examples of clinical cases in which neovascularization routes were reconstructed using the methods of the present disclosure.
Figure 5B:
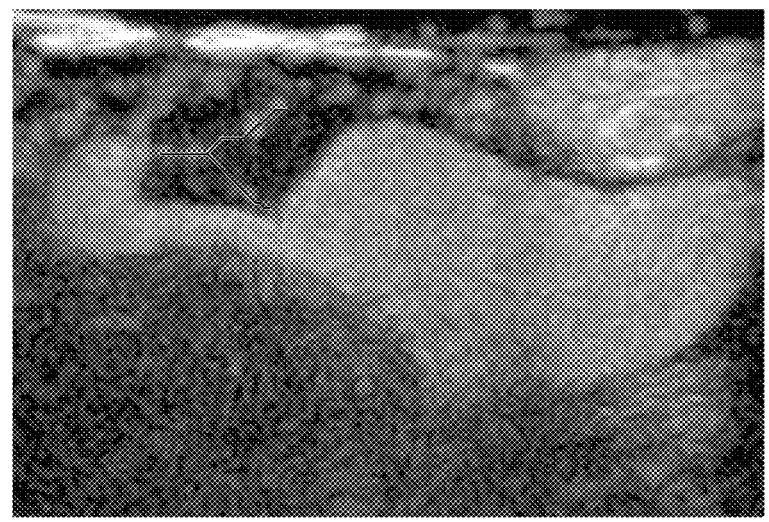

Reference is now made to FIGS. 5A and 5B, which present examples of two clinical cases in which the routes of the neovascularization were reconstructed using the methods of the present disclosure. The carotid artery is shown, with the dark region representing a plaque developed therein. Light regions within this plaque represent imaged segments of the neovascularization flow within the plaque rendered visible by the CEUS. FIG. 5A refers to the case in which one route was detected inside the plaque, while in the case of FIG. 5B two routes were detected.

Figure 6A:
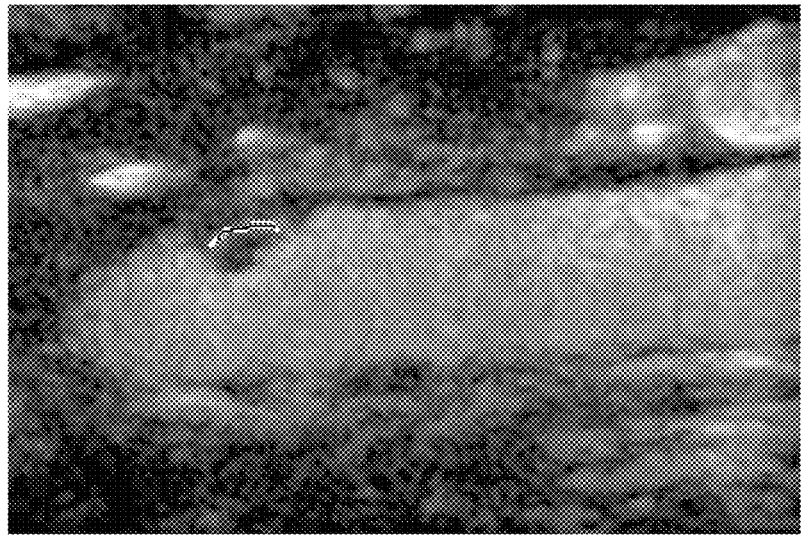
FIGS. 6A and 6B present images of a carotid artery plaque showing the results of semi-automatic and manual reconstructions of neovascularization routes.
Figure 6B:
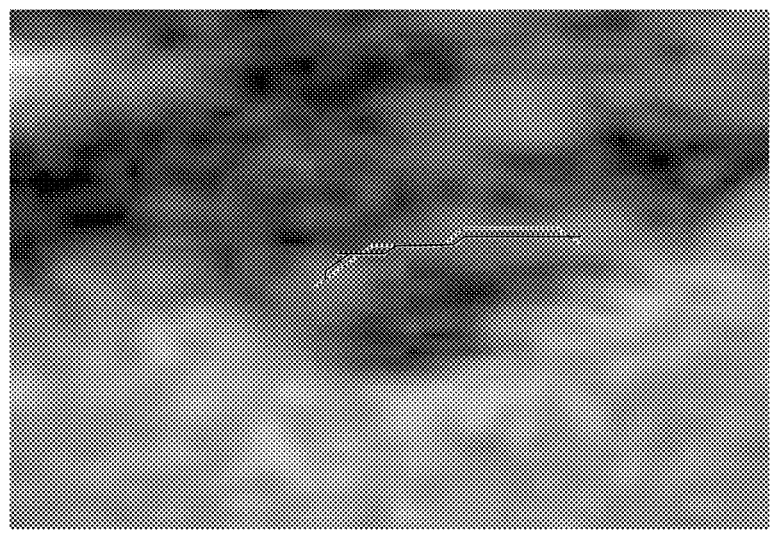

The accuracy with which the route(s) automatically detected by the present method is apparent by comparing the actual paths detected in these images, with a visually estimated path through the light disconnected regions within the plaque. Reference is now made to FIGS. 6A and 6B, which present images of the carotid artery plaque of FIG. 5A, showing a comparison of the results of semi-automatic reconstruction neovascularization routes performed according to the methods of the present disclosure, and manual reconstructions of neovascularization routes. FIG. 6B is a zoomed in image of FIG. 6A, showing the plaque itself and its neovascularization at larger magnification, since the difference between the semi-automatic method of this disclosure, and the manual reconstruction are difficult to resolve in FIG. 6A. The semi-automatic results obtained using the methods of the present disclosure are shown as the full black line, and the manually reconstructed route as the white line. As is observed, the routes are similar except for small deviations. The length of the intra-plaque vessel as detected and calculated by the methods of this disclosure was 0.254 mm with a slope of 12.81 degrees calculated between its start and end points, while the manual marking of the same intra-plaque vessel had a length of 0.247 mm and a slope of 12.26 degrees. The length of the detected vessel—of the order of 0.25 mm.—provides an indication of the resolution attainable by the method of the present disclosure.

Figure 7:
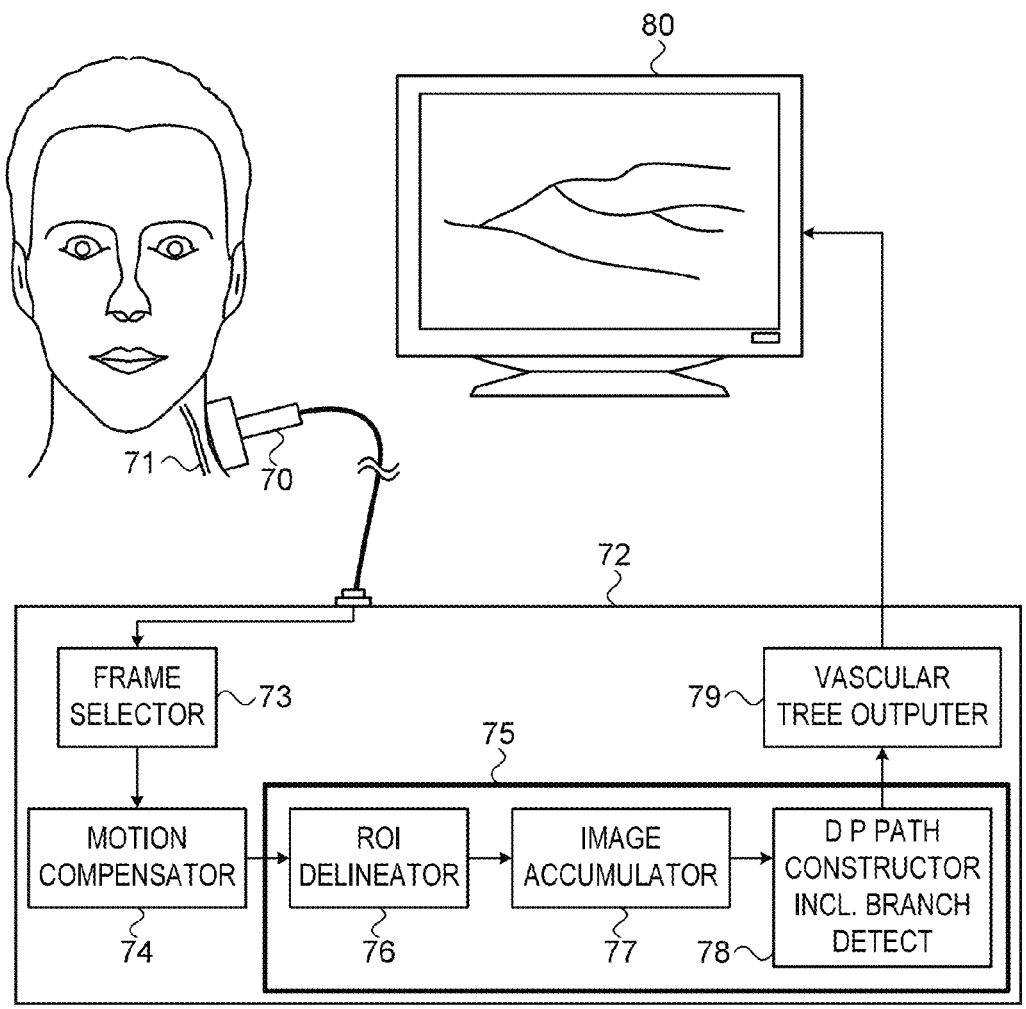
FIG. 7 schematically shows an ultrasound system and its component parts for obtaining the data relating to vascular tree determination and for performing neovascularization quantification of a plaque or tumor.

Finally, reference is now made to FIG. 7, which schematically shows an exemplary system and its component parts for obtaining the data relating to vascular tree determination and for performing neovascularization quantification of a plaque or tumor. The implementation is shown in FIG. 7 for application to a carotid plaque assessment, though it can equally be applied to neovascularization quantification in any other accessible blood vessel or tumor. The system of FIG. 7 is shown configured to perform a complete analysis of the vascular tree, including both image series accumulating and dynamic programming branch plotting, though it is to be understood that the system could also be implemented with only part of the modules shown, as described hereinabove in connection with the various methods of generating the tree. In FIG. 7 the ultrasound transducer 70 is imaging the region 71 to be assessed, and the received images are input to its image processing system 72. This system comprises a number of numerical analysis units, each performing one or more of the functions necessary for generating the data for rendering the vascular tree visible in the images, and for calculating its comparative volume. In one exemplary processing system, the frame selection unit 73 selects a sonar image of the ROI constructed from the received echo signals, and designates the locations within the image showing the presence of contrast material. The imaged information is transferred to a motion compensating module 74 for offsetting the effect of movement of the surrounding tissues from the image obtained. This module may utilize any suitable data manipulation routine, such as a transformation bank method or a particle filter method, or a normalized cross correlation method, and it outputs an essentially static image of the sections of the vasculature imaged, largely independent of limited movements of the surrounding tissue. These motion compensated images are then input to a frame analysis module 75, which incorporates a number of separate calculating modules, including an image processing unit 76 for defining the limits of the region of interest to be quantitatively analyzed, typically using an active contour modeling routine. The frame analysis module also includes a frame accumulator 77 for averaging the separate segments over several frames of the cardiac cycle. Finally, the frame analysis module incorporates a path constructing unit 78, which automatically reconstructs the path of each individual vessel from the discrete segments appearing in the image frames. This path constructing unit is preferably actuated using dynamic programming techniques to provide an output with minimal computing power and in minimum time. In order to include those of the imaged segments not included in the initial paths constructed, a branch detector may also be incorporated within the path constructor to determine when a vessel path being constructed divides into two or more branches, and continues to construct the entire tree taking into account all tributaries of the branched vessel. This branch detector may advantageously incorporate a spatial second derivative detector, which uses the presence of a larger than average second spatial derivatives to detect a potential branching point of the vasculature. Finally, the complete tree output is generated in the output unit 79, where the neovascular concentration is calculated and the results, both graphic and numerical may be displayed on the monitor 80 and stored in memory. It is to be understood that the above described numerical analysis units of the image processing system 72 are only one exemplary implementation of the system, and it is feasible to carry out the vascular tree determination using units with somewhat different functions or different unit nomenclature. However, it is believed that at least the motion compensation module, the path synthesizing unit and the branch detector are the most important parts of the system, for ensuring accurate and speedy generation of the quantization output results.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method of analyzing ultrasound images to provide information regarding neovascularization in a tissue of a subject, said method comprising:
   obtaining a series of contrast enhanced ultrasound images of said tissue;
   compensating for motion of tissue features between different ones of said contrast enhanced ultrasound images, to generate a series of compensated images;
   detecting in at least one of said compensated images discrete segments of imaged contrast material;
   constructing a representation of an arterial tree from said detected segments; and
   quantifying the level of the neovascularization from the extent of the detected segments in said representation of said arterial tree,
   wherein said representation of said arterial tree is constructed by performing dynamic programming on at least one of said series of compensated images.

2. A method according to claim 1, wherein said representation of said arterial tree is constructed by superimposing the positions of said discrete segments of said imaged contrast material from at least two sequential ones of said compensated images, to generate an accumulated image, and detecting segments on said accumulated image, and wherein said dynamic programming is performed on said accumulated image.

3. A method according to claim 1, wherein said arterial tree comprises at least one continuous path between said discrete segments.

4. A method according to claim 1, wherein said quantifying is performed by determining the ratio of the extent of said detected segments in said arterial tree to the imaged area of the tissue in which said neovascularization is to be determined.

5. A method according to claim 1, wherein said compensating for motion of features between different ones of said images is performed by either one of forward tracking or particle filtering methods.

6. A method according to claim 5, wherein said forward tracking method utilizes template matching with a normalized cross correlation criterion.

7. A method according to claim 5, wherein said particle filtering method utilizes a Sum of Absolute Differences (SAD) criterion for each particle.

8. A method according to claim 1, wherein said motion of tissue features comprises at least one of translation, rotation and change of scale of said features.

9. A method according to claim 1, wherein said tissue is either of a plaque or a tumor.

10. A system for providing information regarding neovascularization in a tissue of a subject, said system comprising:
    an ultrasound system for generating a series of contrast enhanced ultrasound images of said tissue;
    a frame analysis unit receiving said images and adapted to designate locations within said images showing the presence of contrast material;
    a motion compensating unit, configured to output a series of compensated images in which the effects of motion of imaged features of said tissue between different ones of said images is cancelled;
    an image processing system comprising:
       a segment detector unit, adapted to detect in at least one of said compensated images discrete segments of imaged contrast material; and
       an arterial tree constructor for outputting a representation of an arterial tree from said detected segments; and
       an output unit using the extent of said detected segments in said representation of said arterial tree to quantify the level of neovascularization in said tissue,
    wherein said arterial tree constructor is configured to perform dynamic programming on at least one of said series of compensated images.

11. A system according to claim 10, wherein said arterial tree constructor is configured to superimpose the positions of discrete segments of said imaged contrast material from at least two sequential ones of said compensated images, to generate an accumulated image, and to detect segments on said accumulated image, and wherein said dynamic programming is performed on said accumulated image.

12. A system according to claim 10, wherein said arterial tree comprises at least one continuous path between said discrete segments.

13. A system according to claim 10, wherein said output unit is adapted to quantify the level of neovascularization in said tissue by determining the ratio of the extent of said detected segments in said arterial tree to the imaged area of the tissue in which said neovascularization is to be quantified.

14. A system according to claim 10, wherein said motion compensating unit is adapted to perform either one of forward tracking or particle filtering methods.

15. A system according to claim 14, wherein said forward tracking method utilizes template matching with a normalized cross correlation criterion.

16. A system according to claim 14, wherein said particle filtering method utilizes a Sum of Absolute Differences (SAD) criterion for each particle.

17. A system according to claim 10, wherein said motion of imaged features of said tissue comprises at least one of translation, rotation and change of scale of said features.

18. A system according to claim 10, wherein said tissue is either of a plaque or a tumor.

* * * * *